United States Patent [19]

Redshaw

[11] 3,985,867

[45] Oct. 12, 1976

[54] IMMUNOASSAYS EMPLOYING A COLORED SECOND ANTIBODY

[75] Inventor: Martin Ralphs Redshaw, Amersham, England

[73] Assignee: The Radiochemical Centre Limited, England

[22] Filed: Dec. 26, 1974

[21] Appl. No.: 536,642

[30] Foreign Application Priority Data
Jan. 2, 1974 United Kingdom.................... 25/74

[52] U.S. Cl. ............................... 424/1.5; 23/230 B; 252/408; 424/12
[51] Int. Cl.[2].................... G01N 33/00; G01T 1/16; G21H 5/02
[58] Field of Search.............. 424/1.5, 12; 23/230 B; 252/408

[56] References Cited
UNITED STATES PATENTS

| | | |
|---|---|---|
| 3,716,632 | 2/1973 | Fader et al............................. 424/1 |
| 3,853,987 | 12/1974 | Dreyer.................................... 424/1 |
| 3,879,262 | 4/1975 | Schuurs et al. .................. 424/12 X |

OTHER PUBLICATIONS

Aach et al., Proceedings of the National Academy of Sciences USA, vol. 68, No. 5, May 1971, pp. 1056–1060.

*Primary Examiner*—Benjamin R. Padgett
*Assistant Examiner*—Christine M. Nucker
*Attorney, Agent, or Firm*—Wenderoth, Lind & Ponack

[57] ABSTRACT

In some radioimmunoassays, the antigen competes with labelled antigen for reaction with a first antibody and the antigen-antibody complex is precipitated by reaction with an aqueous solution of a second antibody to the first antibody. The invention consists in using an artificially colored second antibody, so that the precipitate is easily visible to the naked eye.

3 Claims, No Drawings

IMMUNOASSAYS EMPLOYING A COLORED SECOND ANTIBODY

This invention relates to immunoassays of the kind in which an unknown amount of an antigen to be assayed and a standard amount of a labelled version of the antigen compete for reaction with a standard amount of an antibody. This technique is widely used in the medical field for assaying hormones and other substances.

In practice, the labelled version of the antigen to be determined is most usually a radioactively-labelled compound; but there is no reason in principle why other forms of labelling should not be employed.

The principle of the technique may be represented by the following scheme:

$$C + C^* + R \rightleftharpoons CR + C^*R$$

where
C is the antigen to be assayed,
C* is the labelled version of the antigen, and
R is the antibody.

The amount of R is arranged to be insufficient to react with all of C + C*. As the reaction is, at least to some extent, reversible, an equilibrium is set up in which the ratio of [C*]/[C*]+[C*—R] is determined by the amount of the unlabelled antigen C which is present. If C* is separated from C*—R and the level of activity of each separated part measured, then the value of this ratio is easily calculated.

The amount of the unlabelled antigen C can then be determined in relative or absolute terms, by the use of standard preparations of antigen C, to generate a calibration curve.

The technique is described, with examples, in a Review Paper by R. S. Yalow and S. A. Berson in IAEA-SM-124/106, pages 455–481.

Various techniques are known for separating the bound from the free antigen. One such technique involves the precipitation of the antigen-antibody complex out of solution by the addition of a second antibody directed against the gamma globulin of the animal species used to generate the first antibody. This second antibody may be added either in solution or adsorbed on to an insoluble carrier such as dextran.

Both types of addition suffer from disadvantages. Addition of the second antibody adsorbed on a solid carrier gives rise to difficulties in ensuring that all of the complex has reacted and been precipitated on to the carrier. After removal of the supernatant liquid, the carrier must be thoroughly washed to remove labelled antigen that may have been physically trapped in the carrier without becoming chemically bound to the antibody.

Addition of the second antibody as a solution avoids these mixing and washing problems; but it results in the formation of a minute quantity of whitish or translucent precipitate which may be virtually invisible after centrifuging. Inability to see the solid deposit in the assay tube makes it difficult for an operator, particularly an inexperienced one, to remove the supernatant liquid before measurement of the activity of the deposit. One solution to this problem which has been used is to add extra inert serum, while still using an excess of the second antibody, so as to increase the physical bulk of the precipitate. This solution, however, involves the use of rather large amounts of expensive serum and second antibody. The present invention provides a different (either alternative or additional) solution to this problem, and involves coloring the second antibody, so that precipitate formed is colored and is thus more clearly visible.

The present invention accordingly provides an immuno assay kit comprising:
a. a supply of a labelled version of the antigen to be assayed,
b. a supply of a first antibody to react with the antigen to be assayed,
c. a supply of a second antibody to react with, and remove from solution, a first antibody-antigen complex, characterized in that the second antibody is in a form soluble in water and is artificially colored.

The kit will normally also include a supply of unlabelled antigen for standardisation purposes.

The invention also provides a method of performing an immunoassay, which method comprises the steps of:
i. incubating an aqueous mixture of the antigen to be assayed, a labelled version of the antigen, and a first antibody for the antigen in an amount insufficient to react with all the antigen, and
ii. effecting precipitation of a first antibody-antigen complex by the addition to the aqueous mixture of an aqueous solution of a second antibody which reacts with the said first antibody-antigen complex, so as to form a precipitate, characterized in that said second antibody is artificially colored, so as to form a colored precipitate.

The second antibody is prepared, as is conventional, by introducing some of the first antibody into a second species of animal. Thus, if the first antibody is induced by introducing the antigen into, say, a rabbit, the second antibody may be induced by introducing the rabbit antibody into, say, a donkey. The donkey serum is preferably treated to separate the gamma globulin fraction, since it is only this fraction that is precipitated with the rabbit antibody-antigen complex. (The precipitate is made visible by being brightly colored in a colorless liquid. It is therefore counter-productive to color serum constituents which remain in solution.) The semi-purified gamma globulin fraction is colored by being reacted with a suitable dye. Coloration of biological specimens for visualisation, under the UV microscope, of pathological bacteria and for immunofluorescent histological staining studies, is well known. The nature of the colorants and the coloring techniques is generally not critical to this invention, and conventional colorants and conventional coloring techniques can be used. We prefer to use fluorescin isothiocyanate or Procion Brilliant Red.

The use of fluorescein isothiocyanate for labelling proteins is described by H. Rinderknecht in Nature, London 193, (1962), 167–168.

The use of procion dyes for staining proteins is described by Fazekas de St. Groth, S., Webster, R. G., and Datyner, A. in Biochimica et Biophysica Acta, 71, (1963), 377–91.

(This reference mentions, specifically, the use of procion brilliant blue RS, but the method is applicable to procion red also).

In some instances the dyeing process, or the binding of the dye to the antibodies, inhibits their efficiency in the immunoprecipitation reaction. In such instances it is possible to use a modification of the dyeing method that will protect the active centre of the antibodies.

1. Before dyeing, the second antibody, for example anti-rabbit γ-globulin is purified by extraction onto a solid phase bearing the first antibody, for example rabbit γ-globulin. The solid phase can be sepharose or glass particles.

2. The solid phase is washed to remove all unbound proteins and is then mixed, at the required pH, with the dye. Both solid phase bound rabbit-globulin and second antibody will be dyed, but as they are both bound to each other, the active sites of the antibodies will be protected from being dyed.

3. Excess dye is washed away, together with "damaged" second antibody that has lost the ability to bind onto the immobilised rabbit gamma-globulin.

4. The dyed second antibody is then eluted from the solid phase by by low pH and high salt content. The solid phase is discarded.

The second antibody so prepared will have been dyed while its active binding site for rabbit γ-globulin was blocked and therefore protected from the dye.

The immunoreactivity of this preparation should be unimpaired, and it should react just as well as the natural second antibody.

The nature of the antigen is not critical. The invention is applicable to any antigen which can be assayed by a double antibody immunoassay technique. Exemplary classes of antigen include steroids, protein hormones and peptides. A list of some suitable antigens is given in the article by Yalow and Berson mentioned above. The use of colored second antibodies is likely to be particularly useful for assaying human growth hormone, thyroid stimulating hormone, luteinising hormone, and, more particularly, follicle stimulating hormone (FSH).

The means by which the antigen is labelled is not critical. This is most suitably done by means of a radioactive isotope, but enzyme labelling is a possible alternative.

As solutions of the various reagents are often not stable over prolonged periods, we prefer to provide the reagents in the form of dry, e.g. freeze-dried, solids, which can be reconstituted with water to form buffered solutions. It may be preferable to pre-disperse the labelled antigen, unlabelled antigen where required, and first antibody into the individual assay tubes.

The use of a colored second antibody in place of a white or colorless one does not alter the proportions of the reagents and the other conditions of the immunoassay.

In an experiment, the gamma-globulin fraction of donkey serum, containing antibodies to the first antibody to be used in a FSH immunoassay, was maintained at 1% by weight protein concentration at pH 9 by means of a sodium bicarbonate/sodium chloride buffer. From 1 mg to 10 mg of Procion Brilliant Red dye was added per 100 mg of protein. Dyeing was complete in 30 minutes. Uncoupled dye was removed by passing the solution through a quaternary ammonium polystyrene ion-exchange resin in the chloride form. The resulting dyed gamma globulin was used as the second antibody, according to the method of this invention, in an otherwise conventional FSH immunoassay, and gave rise to a colored precipitate which was clearly visible in the assay tube after centrifuging.

Comparison of performance of the dyed (pink) second antibody with the natural (colorless) second antibody.

Two FSH immunoassays were set up as follows:
1. Standard tubes:
    200μl of appropriate dilution of FSH standard solution plus
    200μl of anti-FSH serum solution.
2. Control serum tubes:
    200μl of control serum plus
    200μl of anti-FSH serum solution.
3. Incubate all tubes at room temperature for 16–20 hours.
4. Add 200μl $^{125}$I-labelled FSH solution to all tubes.
5. Incubate 6–8 hours at room temperature.
6. To one assay (A) add 100μl of dyed second antibody solution (at appropriate dilution) to each tube.
    To the other assay (B) add 100μl of natural colorless second antibody solution (also at the appropriate dilution) to each tube.
7. Incubate overnight at 2° – 4° C
8. Add 1.0ml water to all tubes and centrifuge at 2,000g for 30 minutes.
9. The supernatant liquid in the assay tubes was removed by aspiration. This was easily performed in assay A without the risk of removing the colored precipitates as the latter were clearly visible. Aspiration of the supernatants from above the colorless precipitates in assay B could not be performed with such ease or confidence as the precipitates were virtually invisible.

As an alternative to aspiration, the supernatant solution could be removed by decantation and draining the inverted tubes over a pad of adsorbent paper tissues. Any tubes whose precipitates became dislodged while draining and which might be lost from the tubes could be readily identified in the case of assay A as the precipitates were colored and easily visible, allowing corrective action to be taken while in the case of Assay B, it was virtually impossible to see when the colorless precipitates became dislodged from the assay tubes.

10. After removal of the supernatants, the radioactivity in the tubes was counted and the standard curves drawn for each assay. The FSH concentration of the control sera were obtained by interpolation. Assay A and B gave comparable results for each control serum.

What is claimed is:

1. A method of performing an immunoassay, which method comprises the steps of:
    i. incubating an aqueous mixture of the antigen to be assayed, a labelled version of the antigen, and a first antibody for the antigen in an amount insufficient to react with all the antigen, and
    ii. effecting precipitation of a first antibody-antigen complex by the addition to the aqueous mixture of an aqueous solution of a second antibody which reacts with the said first antibody-antigen complex, so as to form a precipitate, characterized in that said second antibody is artificially colored, so as to form a colored precipitate.

2. A method as claimed in claim 1, wherein the antigen to be assayed is human growth hormone, thyroid stimulating hormone, luteinising hormone or follicle stimulating hormone.

3. Method as claimed in claim 1 wherein the labelled version of the antigen is labelled by means of a radioactive isotope or an enzyme.

* * * * *